(12) United States Patent  (10) Patent No.: US 9,311,276 B2
Jin et al.  (45) Date of Patent: Apr. 12, 2016

(54) METHODS AND APPARATUS FOR ANALYZING TEST DATA IN DETERMINING THE EFFECT OF DRUG TREATMENTS

(71) Applicant: Boehringer Ingelheim International GmbH, Ingelheim am Rhein (DE)

(72) Inventors: Xidong Jin, Southbury, CT (US); Timothy Muir, Brookfield, CT (US)

(73) Assignee: Boehringer Ingelheim International GmbH, Ingelheim am Rhein (DE)

(*) Notice: Subject to any disclaimer, the term of this patent is extended or adjusted under 35 U.S.C. 154(b) by 679 days.

(21) Appl. No.: 13/678,598

(22) Filed: Nov. 16, 2012

(65) Prior Publication Data

US 2013/0158951 A1 Jun. 20, 2013

Related U.S. Application Data

(60) Provisional application No. 61/564,921, filed on Nov. 30, 2011.

(51) Int. Cl.
*G06F 17/18* (2006.01)
*G06F 19/00* (2011.01)

(52) U.S. Cl.
CPC ............ *G06F 17/18* (2013.01); *G06F 19/3443* (2013.01); *G06F 19/363* (2013.01)

(58) Field of Classification Search
CPC ...... G06F 19/18; G06F 17/18; G06F 19/3443
See application file for complete search history.

(56) References Cited

U.S. PATENT DOCUMENTS

| 8,122,073 B2 * | 2/2012 | Jung et al. .................. 600/300 |
| 2011/0112860 A1 * | 5/2011 | Kehr ................................. 705/2 |

* cited by examiner

*Primary Examiner* — Phuong Huynh
(74) *Attorney, Agent, or Firm* — Michael P. Morris; Atabak R. Royaee

(57) ABSTRACT

Methods and apparatus provide for: receiving pre-clinical data measured during drug treatment of a plurality of mammals including at least two treatment groups; performing at least one EXACT, non-parametric, statistical hypothesis test comparing the pre-clinical data for the at least two treatment groups; and performing a Multiple Comparison Procedure (MCP) on the pre-clinical data for at least two comparisons, where the EXACT, non-parametric, statistical hypothesis test and the MCP are conducted on the pre-clinical data to produce one or more p-values, each p-value representing whether an associated one of the treatment groups has experienced a statistically significant improvement or decline in one or more conditions of the mammals associated with the treatment.

20 Claims, 6 Drawing Sheets

EXPERIMENT 1: COMPARISON ARM0 vs ARM2

| STATISTICS | P-VALUE | RESULT |
| --- | --- | --- |
| Para. ANOVA, then Dunnett's | 0.0782 | False Negative |
| Non-Para. ANOVA, then Dunn's | 0.5089 | False Negative |
| Asym. Mann-Whitney, then Bonferroni Correction | 0.0978 | False Negative |
| EXACT Mann-Whitney, then Holm-Bonferroni | 0.0257 | Positive |

FIG. 8

EXPERIMENT 2: COMPARISON ARM0 vs ARM3

| STATISTICS | TIME | P-VALUE | RESULT |
| --- | --- | --- | --- |
| Asym. Mann-Whitney, then Bonferroni Correction | 15 min. | 0.1057 | False Negative |
| Asym. Mann-Whitney, then Holm-Bonferroni | 15 min. | 0.0625 | False Negative |
| EXACT Mann-Whitney, then Holm-Bonferroni | 8.5 days | 0.0413 | Positive |
| Monte Carlo, est. of M-W then Holm-Bonferroni | 15 min. | 0.0426 | Positive |

METHODS AND APPARATUS FOR ANALYZING TEST DATA IN DETERMINING THE EFFECT OF DRUG TREATMENTS

BACKGROUND OF THE INVENTION

The present invention relates to methods and apparatus for analyzing test data in determining the effect (e.g., the efficacy and/or toxicity) of one or more drug treatments in addressing a given pathology. In particular, the methods and apparatus are particularly useful in analyzing data of small sample sizes, data that are non-normally distributed, data that are sparse, skewed, heavily-tied, and/or non-continuous. These types of data exist widely in, but not limited to, non-clinical animal studies.

Conventional data analysis for determining the efficacy of drug treatments involve, among other things, the use of one or more statistical methodologies on measured data taken from living organisms, such as mammal studies (e.g., animal studies, human studies, etc.). In the case of animal studies, the lab animals are provided with a particular drug treatment under evaluation, such as ingesting or otherwise receiving an experimental drug, and various parameters and/or characteristics of the animals (measured data) are collected over a particular period of time. There may be a number of treatment groups in the evaluation, including a control group (receiving a placebo) and one or more additional treatments groups receiving the same or different drug treatments. Each treatment group may be referred to as an "ARM", especially in randomized trials.

The data from the respective ARMS are collected and in some instances the data are manipulated or otherwise processed in order to make them suitable for statistical analysis. The statistical analysis is conventionally applied in order to compare the control ARM to the one or more other ARMS in order to determine whether a given drug treatment ARM has any statistical significance as compared to the control ARM, and whether such difference represents any efficacy as a drug treatment for a particular pathology.

There are many conventional statistical methodologies that have been applied in the analysis of data in drug studies, such as T-tests, analysis of variance (ANOVA) methods, non-parametric ANOVA (such as the Kruskal-Wallis test), the conventional (Asymptotic) Mann-Whitney test, the EXACT Mann-Whitney test, and Multiple Comparison Procedures (MCP) (such as Dunnett's test and Dunn's post test). While these statistical methods have been applied to the drug evaluation process, there are significant problems that may arise when applying a given methodology or set of methodologies to a given drug study. Accordingly, in certain circumstances, the conventional statistical methods and/or application thereof have been found wanting.

Many existing statistical evaluation methods are time consuming and resource demanding. The data sets to be statistically evaluated are often very large and processing times of several hours or even days are common. This is a severe limitation regarding the development of user-interactive statistical analysis application programs. In case it turns out that a particular calculation or sub-calculation, e.g. the execution of one out of a plurality of comparisons of data sets having been derived from different animal groups does not finish for hours or more, the only option left to the user is to stop the whole statistical analysis, thereby loosing results having already obtained from successfully finished sub-calculation steps.

SUMMARY OF THE INVENTION

It has been discovered through theory and experimentation that certain types of drug studies yield data that are not well suited to the conventional statistical methodologies and/or applications. For example, the conventional techniques do not provide satisfactory results when applied to data of relatively small sample sizes (e.g., ten or fewer animals per ARM), data that are non-normally distributed, data that are sparse, skewed, heavily-tied, and/or non-continuous (e.g., ordinal data), such as may be found in non-clinical animal studies. In connection with the instant application, the phrase "pre-clinical data" is defined herein to refer to the above types of data.

By way of example, it has been discovered that conventional application of T-tests are not suitable for evaluating pre-clinical data as defined herein. The so-called T-tests apply parametric analysis, which although acceptable for data having certain characteristics (e.g., normal distribution and continuity), do not provide appropriate analysis of the pre-clinical data as defined herein, which may include non-normally distributed data and/or non-continuous data, among other difficult characteristics.

Additionally, performing multiple pairwise tests is contemplated in accordance with one or more embodiments of the invention. These multiple pairwise tests arise because more than one ARM may be compared to a given control ARM, which introduces the possibility of family-wise type I error. A type I error is a wrong decision that is made when a test rejects a true null hypothesis. A type I error may be compared with a so-called false positive in other test situations. Type I error can be viewed as the error of excessive credulity. The conventional T-tests, however, have no reasonable mechanism to control family-wise type I error.

By way of further example, it has been discovered that conventional application of an ANOVA method followed by an MCP method (such as Dunnett's test) is also not suitable for evaluating pre-clinical data as defined herein. Although an ANOVA method followed by an MCP method may be very popular, and is widely applied in clinical trials, it has been discovered that application of such a conventional technique to pre-clinical data is problematic. Indeed, even though application of an ANOVA method followed by an MCP method may appear more reasonable than the T-test method (because such an approach includes an MCP mechanism to control family-wise type I error), the ANOVA method is nevertheless a parametric analysis. Thus, such methodology does not provide an appropriate analysis of pre-clinical data, which may include relatively small sample sizes, non-normal distributions, sparsity, skew, heavily-tied characteristics, and/or non-continuities.

It has also been discovered that non-parametric versions of ANOVA followed by an MCP method are not suitable for evaluating pre-clinical data as defined herein. A typical approach is to employ the Kruskal-Wallis test (a non-parametric version of a 1-way ANOVA method), followed by Dunn's post test as an MCP method. This approach has become fairly popular because it has been implemented in commercially available software packages, such as GraphPad Prism 5. However, it should be understood that there are no well-accepted MCP methods for the Kruskal-Wallis test. Thus, application of Dunn's post test as an MCP method in this context is highly problematic.

Additionally, through experimentation, it has been discovered that Dunn's post test is unreasonably conservative. One result of such undesirable conservatism is that type II errors may be significantly inflated. A type II error, also known as an error of the second kind, is the wrong decision that is made when a test fails to reject a false null hypothesis. A type II error may be compared with a so-called false negative in other test situations. Type II error can be viewed as the error of excessive skepticism. One of the causes of the conservative outcome of Dunn's post test is that it makes adjustments on raw p-values based on all possible pairs of comparisons of ARM data, not only desired and/or relevant comparisons. Thus, the process is punitive as to such desired and/or relevant comparisons, and results in unnecessarily larger "adjusted" p-values. The larger p-values may lead to false-negative findings in drug discovery, which is an undesirable characteristic.

By way of further example, it has been discovered that conventional application of the conventional (asymptotic) Mann-Whitney test is also not suitable for evaluating pre-clinical data as defined herein. Although the conventional Mann-Whitney test is non-parametric, it is nevertheless asymptotic by nature, i.e., the test can only provide approximate p-values, instead of exact p-values. As a result, any conclusions as to the conventional Mann-Whitney test are subject to error, particularly when the test is applied to pre-clinical data. In addition, the conventional Mann-Whitney test has no reasonable mechanism to control family-wise type I error.

By way of still further example, the conventional wisdom in the art is to avoid the use of the EXACT Mann-Whitney test in connection with application to drug studies. Although the EXACT Mann-Whitney test is recognized as providing exact statistics and resulting in exact p-values (as opposed to mere approximations), the test is notorious in that the execution time is unpredictable and uncontrollable. It has been discovered that it is not unusual for the test to require days to complete even on a small sample size and using a very powerful computer. The accepted wisdom in the art, therefore, has been to avoid using the EXACT Mann-Whitney test in favor of the conventional (asymptotic) Mann-Whitney test. In addition, just as with the conventional Mann-Whitney test, the EXACT Mann-Whitney test has no reasonable mechanism to control family-wise type I error.

In accordance with one or more aspects of the present invention, the undesirable characteristics of the conventional statistical analyses may be avoided, particularly with respect to the pre-clinical data contemplated herein.

Other aspects, features, and advantages of the present invention will be apparent to one skilled in the art from the description herein taken in conjunction with the accompanying drawings.

DESCRIPTION OF THE DRAWINGS

For the purposes of illustration, there are forms shown in the drawings that are presently preferred, it being understood, however, that the invention is not limited to the precise arrangements and instrumentalities shown.

FIG. 4 is a graphical representation of an example of an array of measured data for a given ARM of the drug evaluation program according to one or more further aspects of the present invention;

FIG. 7 is a chart indicating the results of an experiment conducted in accordance with one or more aspects of the present invention; and FIG. 8 is a chart indicating the results of a further experiment conducted in accordance with one or more aspects of the present invention.

DETAILED DESCRIPTION OF THE PREFERRED EMBODIMENTS

Figure 1:
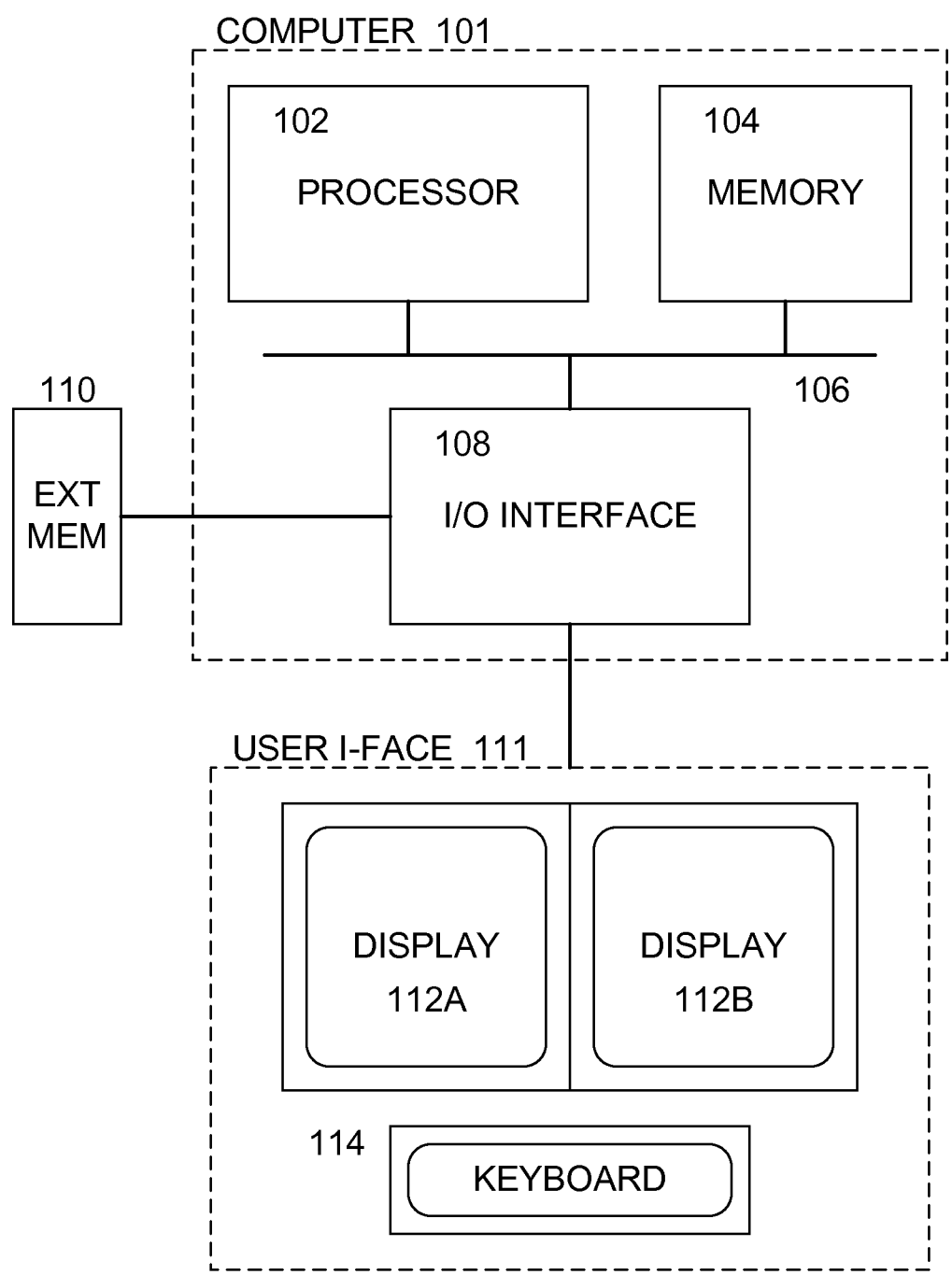
FIG. 1 is a block diagram of a computing system suitable for carrying out statistical data analysis on drug test data in accordance with one or more embodiments of the present invention.

With reference to the drawings, wherein like numerals indicate like elements, there is shown in FIG. 1 a block diagram illustrating an example of a system 100 for analyzing test data in determining the effect (e.g., the efficacy, toxicity, and/or other effect) of one or more drugs and/or drug treatments in addressing a given pathology.

The system 100 preferably includes a computer 101, which includes a data processing unit (or processor) 102 and a memory 104 operatively coupled by way of a data and/or instruction bus 106. The processor 102 may be implemented utilizing any of the known hardware, such as a digital microprocessor, a computer (such as a portable, a stationary and/or a distributed computing system), or any of the other known and/or hereinafter developed data processing units. The memory 104 may be implemented by way of separate hardware or may be disposed within the data processing unit 102, and any of the known hardware and/or software for implementing the memory function may be employed.

Data are preferably input to, and output from, the data processing unit 102 by way of an input/output device (or I/O interface) 108. As will be discussed in detail later herein, a user of the system 100 may desire to input software programs and/or data into the computer 101 by way of an external memory 110 that is coupled to the I/O interface 108 by way of a suitable link (such as a cable, wireless link, etc.) The external memory 110 may be implemented via a flash-drive, disc, remotely located memory device, etc.

The system 100 also includes a user interface device 111, which is operatively coupled to the I/O interface 108 of the computer 101 via a suitable link, such as a cable, wireless link, etc. The user interface device 111 includes one or more displays 112, such as a computer display system employing dual monitors 112A, 112B, as well as an input device 114, such as a keyboard, mouse, voice recognition system, etc. The user of the system 100, such as a researcher, preferably utilizes the user interface device 111 to provide information to the computer 101 in connection with statistically evaluating data obtained during testing of the efficacy, toxicity, etc. of a particular drug and/or drug treatment process. The computer 101 manipulates the data provided by the user using statistical methods and other processes and displays the results thereof on the displays 112 for consideration by the user. In accordance with well-known techniques, the results may also be stored within the memory 104 of the computer 101, output and saved on the external memory device 110, and/or provided to the user in any of a number of other ways.

It is noted that the functional blocks illustrated in FIG. 1 may be partitioned as shown or may be partitioned in any other way, such as in an integral fashion. By way of example, the system 100 may be implemented utilizing a portable, stationary, or distributed computer operating under one or more suitable computer programs. Further, one or more of the functional blocks of the system 100 may be remotely located from the others, such as in a distributed (e.g., networked) system.

Figure 2:
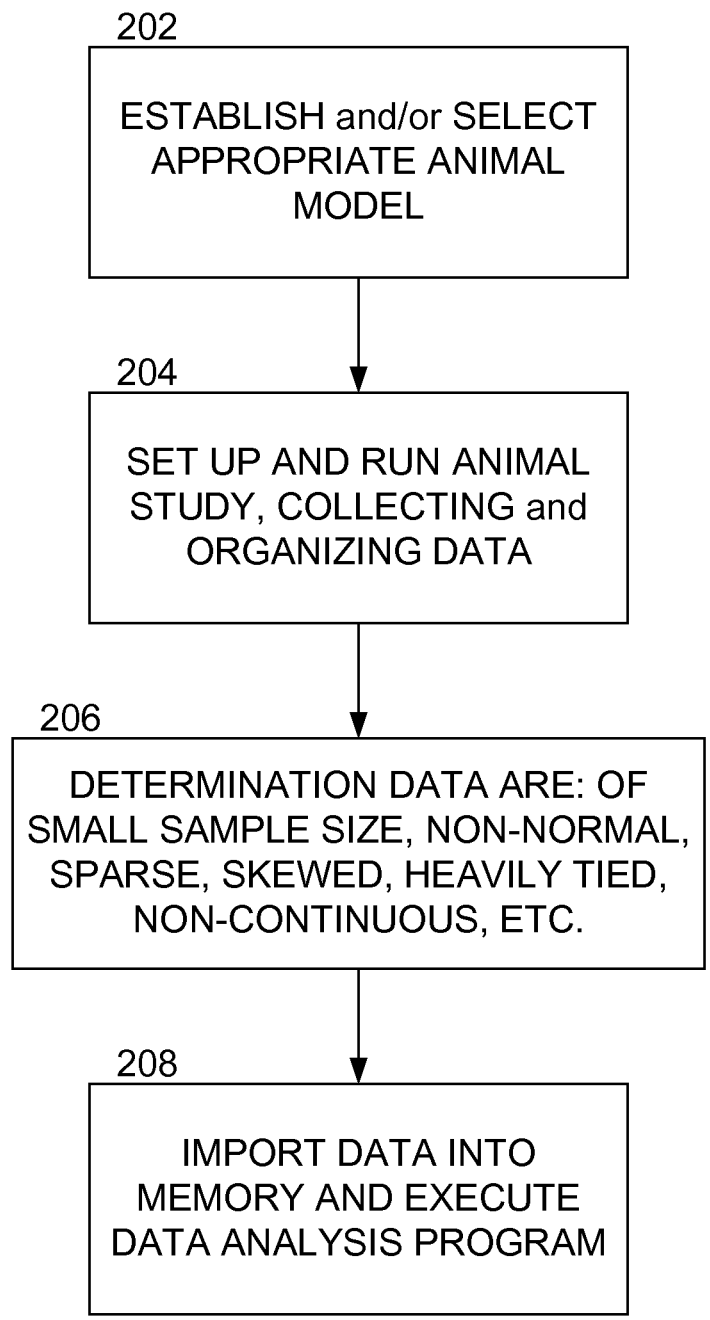
FIG. 2 is a flow diagram indicating certain process steps that may be carried out in accordance with one or more further aspects of the present invention.

Irrespective of how the system 100 is implemented and/or partitioned, it preferably carries out one or more methods for evaluating pre-clinical data obtained by providing a drug (or drugs) to a plurality of mammals under certain circumstances and conditions, and measuring one or more resultant characteristics, parameters, etc. of the mammals. In this regard, reference is now made to FIG. 2, which is a flow diagram indicating certain process steps that may be carried out in accordance with one or more aspects of the present invention. Some of the process steps (actions) illustrated in FIG. 2 may take place prior to using the system 100.

At action 202, a researcher or research team may select an appropriate animal model with which to run animal studies. One such study is the Experimental Autoimmune Encephalomyelitis (EAE), which is an animal model related to brain inflammation. This animal study protocol dictates that certain animals may be used for tests to study human CNS demyelinating diseases, including Multiple Sclerosis, acute disseminated encephalomyelitis (ADEM), T-cell-mediated autoimmune disease, and others. EAE may be induced in any number of animal species, including mice, rats, guinea pigs, rabbits, primates, etc.

At action 204, the animals are subjected to certain tests and data are collected. For example, in an EAE study the animals are subject to one or more antigens, which result in the animals exhibiting certain disease characteristics regarding both immunology and pathology. The animals will display symptoms within a certain amount of time, which may be measured in connection with receiving drug treatment. In a preferred scenario, one treatment group of animals is a control group, which receives a placebo, and one or more other treatment groups of animals receive differing drug treatments.

Figure 3:
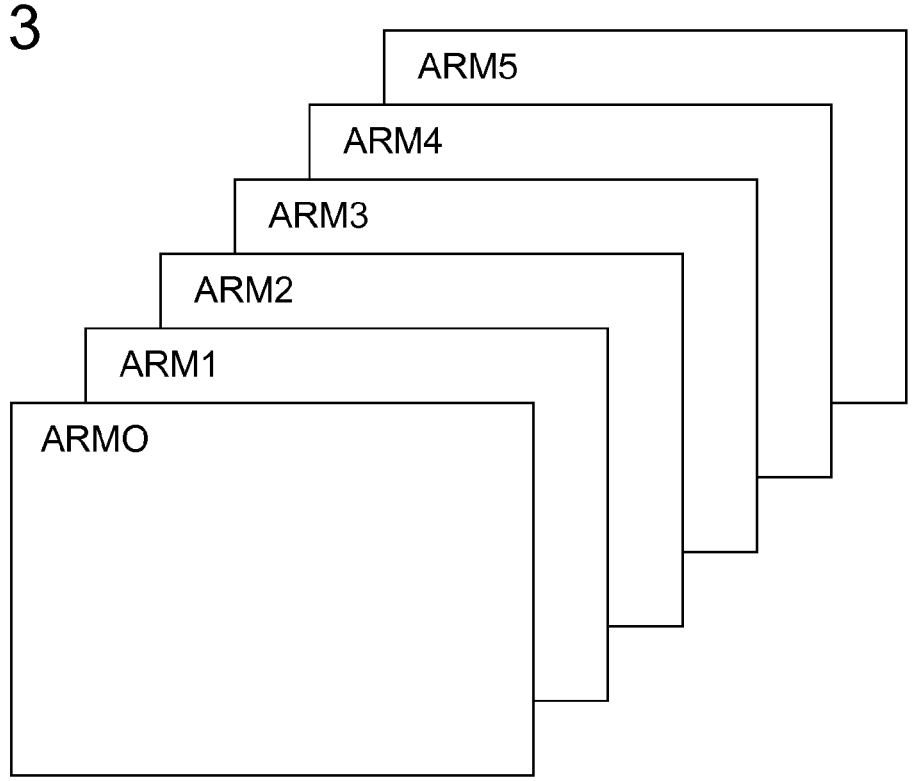
FIG. 3 is a graphical representation of the collection of data from one or more living organisms in accordance with a drug evaluation program according to one or more further aspects of the present invention.

As illustrated in FIG. 3, each treatment group is organized into an ARM, for example one of six ARMS (ARM0-ARM5), with ARM0 being the control group. The measured data may be collected from the respective treatment groups over a specified time period, resulting in a time series of data. FIG. 4 illustrates an array of measured data (DATAm,n) collected for a given ARMi. The illustrated ARMi includes ten animals (Animal 0-Animal 9), and a number of provided and/or measured parameters for each animal. One of the columns of data is labeled "Description" in FIG. 4, which represents an example or characteristic or description of the drug treatment for the given treatment group. Each treatment group may have the same or a differing drug dose or other drug treatment characteristics. The measured parameters (for example, Param 1-Param 4) represent the measured data obtained from the animals of the treatment group over the duration of the test. These parameters may be any suitable parameters and may include aggregates, such as one number representing a plurality of measurements over the course of the test. One such aggregate may employ the so-called Area Under the Curve (AUC) algorithm to compute one number representing more than one measurement over the test. Other aggregates may include maxima, minima, averages, RMS values, etc.

Turning again to FIG. 2, at action 206 the researcher may determine that the measured data are (or are likely to be) of a character in which application of conventional statistical techniques may be problematic. As discussed earlier, the features of the various embodiments of the invention have been developed in order to improve the results obtained by analyzing pre-clinical data as compared with conventional techniques. Again, as used herein the pre-clinical data may include one or more of the following characteristics: relatively small sample sizes; non-normally distributed; sparsity; skew; heavily-tied; and/or non-continuous. If such a determination is affirmative, then the researcher may choose to import the pre-clinical data into the system 100 (action 208) and execute one or more methods in accordance with the present invention to analyze the efficacy, and/or toxicity, etc. of the drug treatments employed during the animal study.

Figure 5:
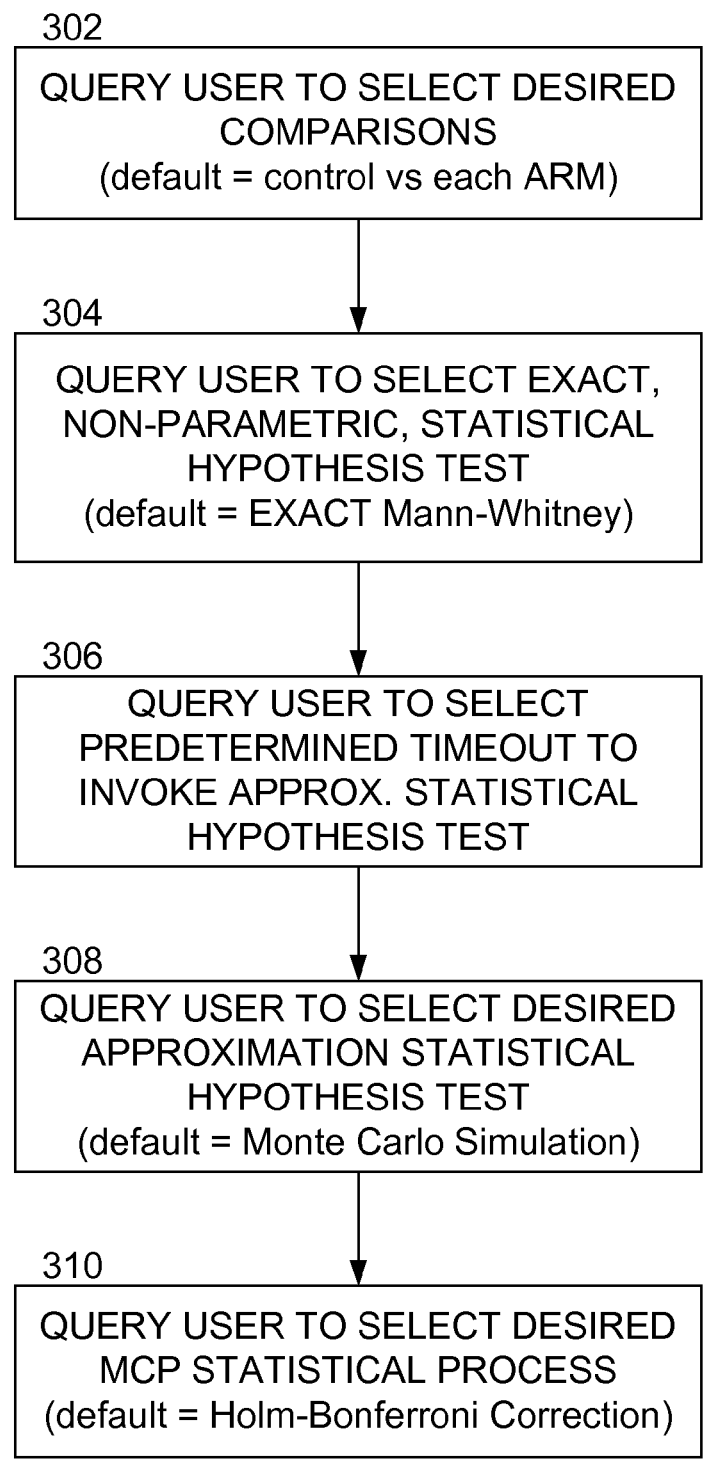
FIG. 5 is a flow diagram indicating alternative and/or additional process steps that may be carried out in accordance with one or more further aspects of the present invention.
Figure 6:
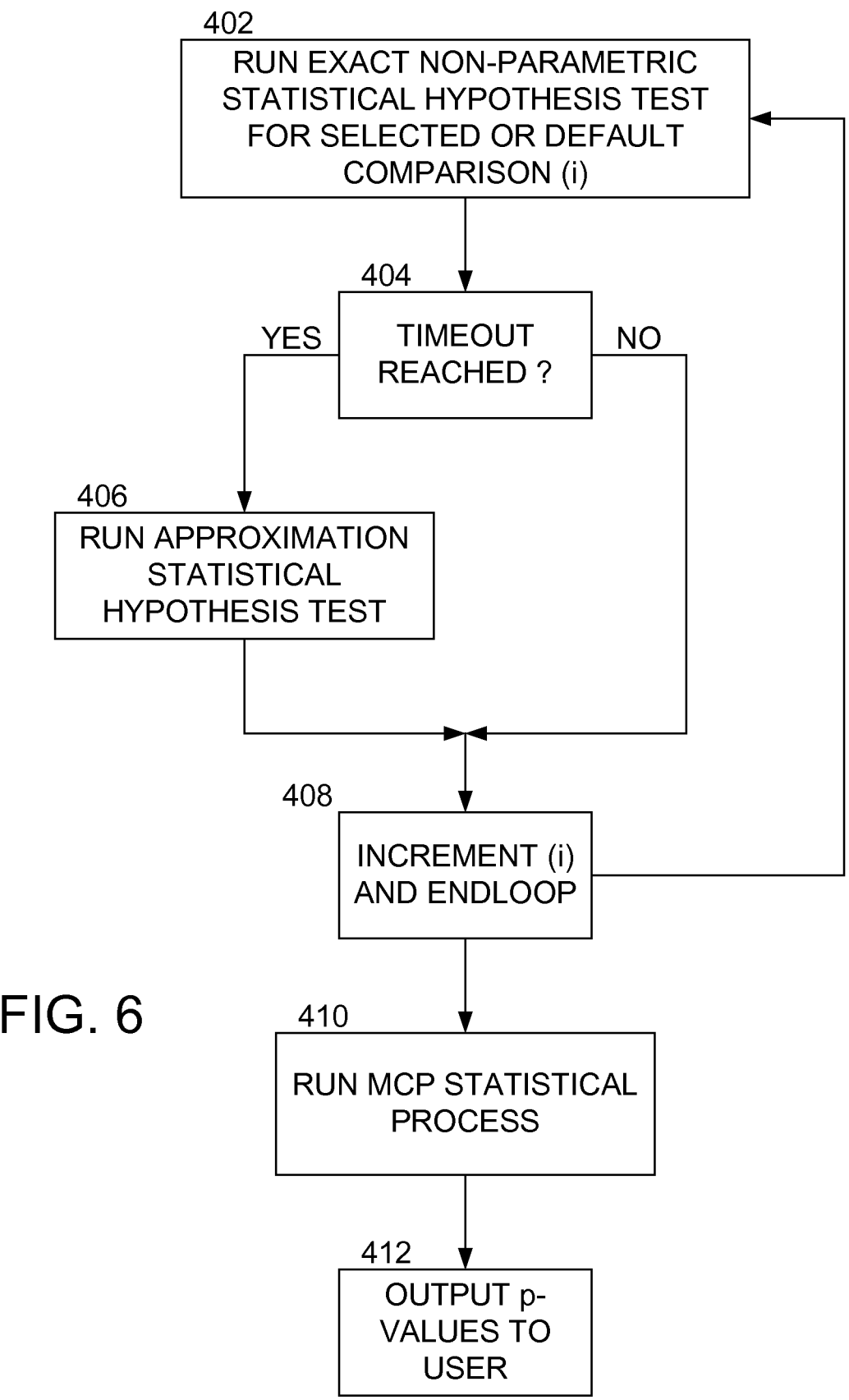
FIG. 6 is a flow diagram indicating further alternative and/or additional process steps that may be carried out in accordance with one or more further aspects of the present invention.

Assuming that the researcher has decided to employ the system 100 to analyze the pre-clinical data gathered during the animal studies, reference is now made to FIGS. 5 and 6, which are flow diagrams indicating alternative and/or additional process steps that may be carried out in accordance with one or more aspects of the present invention.

It is preferred that the software program running on the system 100 is operable to provide the researcher (user) with some control in influencing the scope and direction of the statistical analysis. For example, at action 302 the system 100 may optionally query the user (via a graphical user interface, not shown) on the display 112A, 112B for input related to which comparisons to run. In this regard, it is understood that a "comparison" is the process of executing a statistical comparison test (or tests) as between the respective data obtained from two different ARMs. In a non-clinical animal study it is often the case that more than one pair of simultaneous comparisons is required to determine whether the results of respective ARMs are significantly different. For example, the researcher may wish to determine whether there are significant differences between the control group and any one or more of: (i) a treatment group receiving a low-dose of the drug(s) of interest, (ii) a treatment group receiving a middle-dose of the drug(s) of interest, and (iii) a treatment group receiving a high-dose of the drug(s) of interest. If the comparisons are relevant and informative, the researcher may use the results of the statistical analysis to determine the efficacy, toxicity, etc. of a particular drug treatment.

The system 100 provides the researcher with the opportunity to pre-select which comparisons are to be executed (and by implication which comparisons are not to be executed). Thus, the user may specify that each of the ARMS 1 through ARM 5 is compared to the control ARM 0, thereby yielding five comparisons and five p-values. Alternatively, the user may specify that each of the ARMS 1 through ARM 3 is to be compared to the control ARM 0 and no others, etc. This tailoring of (in some cases limiting of) the comparisons advantageously reduces unnecessary computation, thereby reducing the time needed to perform the statistical analysis. By contrast, many conventional statistical approaches do not provide the researcher with the flexibility in pre-selecting the comparisons, which may result in excessive execution time and in many cases failure to achieve a result even after many days of computation. More importantly, comparing all possible pairs of ARMs without pre-selecting the only desired and/or relevant comparisons can increase the likelihood of a false negative error, which is highly undesirable in drug discovery.

At action 304, the software program running on the system 100 may optionally provide the researcher with some additional control to influence the statistical analysis. In particular, the system 100 may query the user (via the graphical user interface, not shown) on the display 112A, 112B for input related to which statistic test he/she wishes to utilize in the process. In this regard, further reference is made to action 402 (FIG. 6), where the software running on the system 100 causes the processor 102 to execute a statistical hypothesis test on the one or more comparisons (such as the comparisons selected at action 302, or one or more default comparisons, etc.). As noted above, the comparison would be conducted on the pre-clinical data for at least two treatment groups (e.g., ARM0 and ARM1). It is preferred that the statistical hypothesis test is of a particular type, namely, at least one EXACT, non-parametric, non-asymptotic, statistical hypothesis test. An "EXACT non-parametric (statistical hypothesis) test" as used herein is a statistical algorithm that does not employ asymptotic and/or approximate statistical methods and does not make any distributional assumptions concerning the data being analyzed. By way of example, the statistical hypothesis test may be taken from the group consisting of: the EXACT Mann-Whitney test, and the EXACT Kruskal-Wallis test, where EXACT Mann-Whitney test is preferred. Other names for the EXACT Mann-Whitney test include the EXACT Mann-Whitney U test, the EXACT Mann-Whitney-Wilcoxon test, and the EXACT Wilcoxon rank-sum test.

Accordingly, at action 304, the user may be given the option of selecting the specific test through manipulation of the user interface 111.

Reference is now made to action 306 (FIG. 5) and actions 404 and 406 (FIG. 6). It has been discovered that the use of at least one EXACT, non-parametric, non-asymptotic, statistical hypothesis test may be highly beneficial in connection with running statistical comparisons on the pre-clinical data having the characteristics discussed herein. However, it has also been discovered that the use of such a test may sometimes come at a significant cost, particularly when the cost is measured in the time it takes to run the test. For example, running the EXACT Mann-Whitney test has been found to require an uncertain amount of time to complete (even with a powerful computer 101), sometimes requiring many days to complete.

A solution to this problem has been found, however, by providing the user with further control to influence the statistical analysis. In particular, at action 306 (FIG. 5) the system 100 may query the user (via the graphical user interface, not shown) on the display 112A, 112B for input related to a predetermined timeout period. (In alternative embodiments, the timeout period may be a default value, such as some number of minutes, hours, etc.) In operation, the system 100 continues to perform the EXACT, non-parametric, statistical hypothesis test on the pre-clinical data (action 402, FIG. 6) so long as the timeout period has not expired. Thus, at action 404 the system 100 monitors an amount of time that elapses during the performance of the statistical hypothesis test and makes a determination as to whether the timeout (the predetermined threshold) has been reached. If the determination is in the negative, then the process flow continues to execute the statistical hypothesis test on the pre-clinical data (action 402) or if such test is complete, the process flow continues to action 408 (which will be discussed later).

If the determination is in the affirmative (i.e., the timeout has been reached), then the process flow advances to action 406, where the performance of the EXACT, non-parametric, statistical hypothesis test on the pre-clinical data is interrupted. Proximate to such interruption, the system 100 instead performs an approximation statistical hypothesis test on the pre-clinical data. An "approximation statistical hypothesis test" as used herein is a statistical algorithm that does employ asymptotic and/or approximate statistical methods to perform the EXACT non-parametric (statistical hypothesis) test. A preferred approximation is the Monte Carlo simulation/estimation method. In this regard, at action (308, FIG. 5) the system 100 may optionally provide the user with the ability to select the type of approximation statistical hypothesis test by querying the user (via the graphical user interface, not shown) on the display 112A, 112B to enter a selection. If a default is implemented, then the Monte Carlo simulation method is preferred.

The process flow indicated at action 408, with an incrementing end-loop function, is intended to schematically illustrate that the statistical hypothesis tests are conducted on the pre-clinical data to produce statistical data (raw p-values) on each of a plurality of comparisons, such as ARM1 compared with ARM0, ARM2 compared with ARM0, ARM3 compared with ARM0, etc. A p-value is the probability of obtaining a test statistic at least as significant as the one that was actually observed, assuming that the null hypothesis is true. One often rejects the null hypothesis when the p-value is less than the significance level $\alpha$ (Greek alpha), which is often predetermined to be 0.05 or 0.01. When the null hypothesis is rejected, the result is said to be statistically significant. When the system 100 outputs a p-value that is less-than $\alpha$ (e.g., $\alpha=0.05$) as to a particular comparison, then it is determined that the comparison is statistically significant, i.e., that a positive result has obtained and there is strong statistical evidence to support that the particular drug treatment at issue has had some effect (e.g., efficacy, toxicity, etc.) as compared with a particular reference (such as the control treatment group, ARM0). In contrast, when the system 100 outputs a p-value that is greater-than $\alpha$ as to a particular comparison, then it is determined that the comparison is not statistically significant, i.e., that a negative result has obtained and there is not sufficient evidence to support that the particular drug treatment at issue has had any efficacy, toxicity, etc. as compared with a particular reference.

In a non-clinical animal study it is often the case that multiple (and usually simultaneous) comparisons are required to determine whether the results of respective ARMs are significantly different. For example, the researcher may wish to determine whether there are significant differences between the control group (ARM0) and any one or more of other groups, such as: (i) a treatment group receiving a low-dose of the drug(s) of interest, (ii) a treatment group receiving a middle-dose of the drug(s) of interest, and (iii) a treatment group receiving a high-dose of the drug(s) of interest. In such situations, a Multiple Comparison Procedure (MCP) is preferred to adjust the raw p-values (the resultant statistics of the statistical hypothesis tests) to control the family-wise type I error to ensure the statistics are reliable.

It should be noted that the respective comparisons performed via actions 402, 404, 406, 408 may or may not trigger the time-out at action 404. Thus, the results (raw p-values) of all the comparisons may include at least one p-value produced via the EXACT, non-parametric, statistical hypothesis test and/or at least one p-value produced via the Monte Carlo approximation. The resulting set of raw p-values is the output of action 408, irrespective of which statistics produced each given p-value.

In this regard, the process flow eventually advances to action 410 (FIG. 6), where an MCP is run on the statistical results (from actions 402, 404, 406, 408), e.g., run on at least two comparisons resulting from the EXACT, non-parametric, statistical hypothesis test and/or the Monte Carlo approximation. As with some of the other parameters, it is preferred that the user be given the opportunity to specify which MCP is employed by the system 100. Thus, at action 310 (FIG. 5), the system 100 may prompt the user (via the graphical user interface, not shown) on the display 112A, 112B to select the MCP of his/her choice. By way of example, the MCP may be taken from the group consisting of the Holm-Bonferroni Correction, the Bonferroni Correction, the false discovery rate (FDR) correction, and the Benjamini-Hochberg Correction. One of these MCPs (or some other suitable MCPs) may be established as a default by the system 100; however, the Holm-Bonferroni Correction is preferred.

The process flow after action 410 results in one or more p-values (action 412), final p-values. A "final p-value" as used herein is a p-value (or "raw p-value") having been corrected for controlling the family-wise type-I error rate by applying an MCP, e.g., the Holm-Bonferroni Correction or others. Each final p-value represents whether an associated one of the treatment groups has experienced a statistically significant effect, e.g., an improvement or decline in one or more conditions of the mammals associated with the treatment (showing efficacy of the treatment, some toxicity, etc.).

Reference is now made to FIG. 7, which is a chart indicating the results of a hypothetical experiment (EXPERIMENT 1), conducted in accordance with one or more aspects of the present invention. This experiment is based on some hypothetical test conditions, hypothetical pre-clinical data, and hypothetical p-values. It is noted, however, that the hypothetical experiment has some basis in actual animal tests. The hypothetical experiment is based on an Experimental Autoimmune Encephalomyelitis (EAE) animal model for Multiple Sclerosis. The sample size is small (e.g., ten animals per treatment group), the data are ordinal, non-normal, and non-continuous. Additionally, the data is considered sparse, skewed, and/or heavily-tied by its nature.

FIG. 7 illustrates the p-values obtained by different statistical approaches when comparing a control group (ARM0) with treatment groups, such as a low-, middle-, or high-dose drug-treated group (ARM1-3). Note only resultant p-values of ARM0 versus ARM2 are illustrated here. When the comparison is conducted using the parametric, ANOVA test, followed by Dunnett's test, the resultant p-value is 0.0782. This value represents a false negative because the known efficacy of the drug treatment profile associated with ARM2 is positive. The false negative is the consequence of employing a conventional statistical technique on pre-clinical data (as defined herein). When the comparison is conducted using the conventional non-parametric, ANOVA test, followed by Dunn's test, the resultant p-value is 0.5089, which again is a false negative. Further, when the comparison is conducted using the conventional (asymptotic) parametric, Mann-Whitney test, followed by Bonferroni Correction, the resultant p-value is 0.0978, which once again is a false negative. However, in accordance with one or more aspects of the present invention, when the system 100 is used (without the timeout option being employed and/or invoked), the non-parametric, non-asymptotic, EXACT Mann-Whitney test is performed, followed by the Holm-Bonferroni MCP method, which yields a p-value of 0.0257. This positive result is the correct result for ARM2.

Reference is now made to FIG. 8, which is a chart indicating the results of a further hypothetical experiment (EXPERIMENT 2), conducted in accordance with one or more aspects of the present invention. This experiment is also based on some hypothetical test conditions, hypothetical pre-clinical data, and hypothetical p-values. Again, like EXPERIMENT 1, the hypothetical experiment has some basis in actual animal tests. In this regard, while FIG. 7 illustrates the p-values obtained by statistically comparing ARM0 and ARM2, FIG. 8 may be considered to be the p-value results obtained by statistically comparing ARM0 and ARM3 (which may be a different low-, middle-, or high-dose drug-treated group).

When the comparison is conducted using the conventional (asymptotic) Mann-Whitney test, followed by the Bonferroni correction, the resultant p-value is 0.1057. This is a false negative because the known efficacy of the treatment profile associated with ARM3 is positive. The false negative is the consequence of employing a conventional statistical technique on pre-clinical data (as defined herein). When the comparison is conducted using the conventional (asymptotic) Mann-Whitney test, followed by the Holm-Bonferroni Correction, the resultant p-value is 0.0625, which again is a false negative. It is noted that each of the above conventional techniques was completed in only 15 minutes, which is a relatively short, and desirable period of time. Of course, the fact that the conventional techniques produced incorrect results is a fairly large disadvantage, which outweighs the desirability of a short computation length.

When the comparison is conducted using the system 100 according to one or more aspects of the invention (with no timeout period invoked), the non-parametric, non-asymptotic, EXACT Mann-Whitney test is conducted, followed by the Holm-Bonferroni correction. The resultant p-value is 0.0413, which is a positive and is the correct result for ARM3. The amount of time to run this analysis, however, takes 8.5 days. This is a rather lengthy amount of time, even considering that the correct result is obtained. Finally, when the comparison is conducted using the system 100 (with the timeout period invoked), a kind of non-parametric, non-asymptotic, EXACT Mann-Whitney test is conducted and a determination is made that the timeout period has elapsed (when the EXACT Mann-Whitney test is interrupted and instead the Monte Carlo estimation method is invoked), followed by the Holm-Bonferroni method. The resultant p-value is 0.0426, which is a positive; indeed, when compared to the p-value of 0.0413 obtained after 8.5 days of running the EXACT Mann-Whitney test, it is a stunning result. Moreover, the execution of the Monte Carlo estimation method followed by the Holm-Bonferroni method to obtain the p-value of 0.0426 is completed in 15 minutes. Thus, the correct result is obtained in a relatively short period of time.

The skilled artisan will appreciate from the above description and referenced drawings that many combinations of elements, features, steps, etc. may be achieved in accordance with various embodiments of the invention. Some of these combinations are listed below.

In accordance with one or more further embodiments of the present invention, a computer-implemented method may comprise: (a) receiving pre-clinical data acquired from a plurality of mammals treated with a drug, the plurality of mammals comprising at least two treatment groups; (b) determining one or more comparisons, wherein each comparison is indicative of two sub-sets of the received pre-clinical data, each sub-set having been obtained from one of the at least two treatment groups; (c) determining at least one EXACT, non-parametric, statistical hypothesis test; (d) automatically starting, for each of the one or more determined comparisons, to perform the determined at least one EXACT, non-parametric, statistical hypothesis test by comparing the two sub-sets of pre-clinical data indicated by said comparison for calculating a first result for each of said one or more comparisons, wherein each of the first results comprises a raw p-value; (e) performing a Multiple Comparison Procedure taking the first results as input, said Multiple Comparison Procedure transforming each of the raw p-values into a final p-value, each final p-value representing, given a level of significance, whether one of the treatment groups associated with any of the comparisons has experienced a statistically significant improvement or decline in one or more conditions of the mammals associated with the treatment; (f) generating a signal being indicative of the one or more final p-values; and (g) outputting the signal.

The preceding combination features may be advantageous, because by applying the MCP on the raw p-values, final p-values are calculated which have been corrected for controlling the family-wise type-I error rate.

The computer-implemented method according to the preceding combination of features may further include that the step of outputting comprises displaying the calculated one or more final p-values or an indication of the statistically significant improvement or decline via a GUI of an application program.

The computer-implemented method according to the features of anyone of the previous combinations may further include that the pre-clinical data has one or more of the following properties: sparsely distributed; skew distributed; heavily-tied distributed; non-normal distributed; and small-sized, wherein a small sized data set is a data set comprising less than 11 elements.

The computer-implemented method according to the preceding combination may further include, for each of the one or more comparisons: (a) monitoring an amount of time elapsing during the start of performing the determined at least one EXACT, non-parametric, statistical hypothesis test; (b) determining whether the amount of time exceeds a timeout value; (c) if the amount of time does not exceed the timeout value, completing the performance of the determined at least one EXACT, non-parametric, statistical hypothesis test and returning one of the first results; (d) if the amount of elapsed time exceeds the timeout value: (i) interrupting the performance of the at least one determined EXACT, non-parametric, statistical hypothesis test; and (ii) automatically performing an approximation statistical hypothesis test by comparing the two sub-sets of the received pre-clinical data indicated by each of the one or more determined comparisons for calculating a second result, the second result comprising a raw p-value; (e) performing the Multiple Comparison Procedure on the first and second results; and (f) performing the Multiple Comparison Procedure taking the first and second results as input, said Multiple Comparison Procedure transforming each of the raw p-values of the first and second results into a final p-value.

The computer-implemented method of the preceding combination may further include that the selected approximation statistical hypothesis test is a Monte Carlo simulation method.

The computer-implemented method of anyone of the previous combinations may further include that the EXACT, non-parametric, statistical hypothesis test is taken from the group consisting of: the EXACT Mann-Whitney test, and the EXACT Kruskal-Wallis test.

The computer-implemented method of anyone of the previous combinations may further include that the EXACT, non-parametric, statistical hypothesis test is the EXACT Mann-Whitney test.

The computer-implemented method of anyone of the previous combinations may further include that the Multiple Comparison Procedure is taken from the group consisting of the Holm-Bonferroni Correction, the Bonferroni Correction, the false discovery rate (FDR) correction, and the Benjamini-Hochberg Correction.

The computer-implemented method of anyone of the previous combinations may further include that the Multiple Comparison Procedure is the Holm-Bonferroni Correction test.

The computer-implemented method of anyone of the previous claims, wherein the pre-clinical data is received from a data source, the data source being selected from the group consisting of: a lab-device, a laboratory information management system (LIMS) or a computer readable storage medium.

The computer-implemented method of anyone of the previous combinations may further include any one or more of that: (i) the one or more comparisons are determined by prompting a user of the application program via the graphical user interface to select one or more comparisons from a plurality of comparisons available for all subsets of the received pre-clinical data, and/or (ii) the determined at least one EXACT, non-parametric, statistical hypothesis test is determined by prompting the user via the GUI to select at least one of a plurality of EXACT, non-parametric, statistical hypothesis tests; and/or (iii) the performed Multiple Comparison Procedure is determined by prompting the user via the GUI to select one of a plurality of available Multiple Comparison Procedures; (iv) the timeout value is predetermined timeout value or is specified by the user via the graphical user interface; and (v) upon having determined the one or more comparisons and the at least one EXACT, non-parametric, statistical hypothesis test, the performance of the determined at least one EXACT, non-parametric, statistical hypothesis test is automatically started.

The computer-implemented method according to the preceding combination may include that the approximation statistical hypothesis test is determined by prompting the user via the graphical user interface to select one approximation statistical hypothesis test from a plurality of available approximation statistical hypothesis tests.

The computer-implemented method according to anyone of the previous combinations may further include that the plurality of mammals comprises at least three treatment groups and wherein at least two comparisons are determined.

The computer-implemented method of anyone of the previous combinations may further include: (a) storing the receive pre-clinical data, the received pre-clinical data having been derived from a first pre-clinical study, in association with an indication of the selected one or more comparisons and in association with an indication of the determined at least one EXACT, non-parametric, statistical hypothesis test in a queue element of a batch job queue; (b) receiving further pre-clinical data, the further pre-clinical data having been acquired from a plurality of said or other mammals treated with a drug in a further pre-clinical study; (c) repeating the step of prompting the user via the GUI to select one or more further comparisons for the received further pre-clinical data and repeating the step of prompting the user via the GUI to select one out of the plurality of EXACT, non-parametric, statistical hypothesis tests for determining one or more further comparisons and for determining at least one further EXACT, non-parametric, statistical hypothesis test for said further pre-clinical data; (d) storing the further pre-clinical data of the further pre-clinical study in association with the one or more determined further comparisons and in association with the at least one determined further EXACT, non-parametric, statistical hypothesis test in a further queue element of the batch job queue; (e) repeating steps b) to d) until no further pre-clinical data is received or upon a loop termination signal is received; and (f) automatically executing the batch job queue, wherein upon execution of each batch queue element the execution of the respectively determined at least one EXACT, non-parametric, statistical test is automatically started on the two data sub-sets indicated by each of the one or more further comparisons of said batch job queue element.

The computer-implemented method according to the preceding combination may further include: (g) that executing the step c) further comprises prompting the user via the GUI to select a further predefined timeout value or to specify a further user-specific timeout value for the further pre-clinical data; (h) that executing the step c) further comprises prompting the user via the GUI to select a further one of a plurality of approximation statistical hypothesis tests; (i) that executing the step d) further comprises storing the further pre-clinical data in association with said timeout value and in association with an indication of said further selected approximation statistical hypothesis test in said further queue element; (j) that executing the step f) for any of the batch job queue elements further comprises, for each of the one or more further comparisons of said element: (1) monitoring an amount of time elapsing during the start of the further EXACT, non-parametric, statistical hypothesis test on the further pre-clinical data stored in a currently executed batch job queue element; (2) determining whether the amount of time exceeds the further timeout value; (3) if the amount of time does not exceed the further timeout value, completing the performance of the further selected at least one EXACT, non-parametric, statistical hypothesis test; and (4) if the amount of elapsed time exceeds the further timeout value: (4a) interrupting the performance of the at least one further determined EXACT, non-parametric, statistical hypothesis test; and (4b) automatically performing the selected further approximation statistical hypothesis test by comparing the two sub-sets of the received pre-clinical indicated by said comparison for calculating a further second result, the second result comprising a raw p-value; and (k) performing the Multiple Comparison Procedure on the one or more first and second further results for calculating a final p-value for each of the further comparisons obtained for said batch job queue element.

In accordance with one or more further embodiments of the present invention, a computer-readable storage medium may comprise instructions which, when executed by a processor, causes the processor to execute the steps of anyone of the previous combinations.

In accordance with one or more further embodiments of the present invention, a data processing system may comprise: a processor; a first interface for receiving pre-clinical data from a data source, the pre-clinical data having been acquired from a plurality of mammals treated with a drug, the plurality of mammals comprising at least two treatment groups; a display means; a computer-readable storage medium comprising instructions which, when executed by the processor, cause the processor to execute an application program, the application program being adapted for: (i) determining one or more comparisons, wherein each comparison is indicative of two sub-sets of the received pre-clinical data, each sub-set having been obtained from one of the at least two treatment groups; (ii) determining at least one EXACT, non-parametric, statistical hypothesis test; (iii) automatically starting, for each of the one or more determined comparisons, to perform the determined at least one EXACT, non-parametric, statistical hypothesis test by comparing the two sub-sets of pre-clinical data indicated by said comparison for calculating a first result for each of said one or more comparisons, wherein each of the first results comprises a raw p-value; (iv) performing a Multiple Comparison Procedure taking the first results as input, said Multiple Comparison Procedure transforming each of the raw p-values into a final p-value, each final p-value representing, given a level of significance, whether one of the treatment groups associated with any of the comparisons has experienced a statistically significant improvement or decline in one or more conditions of the mammals associated with the treatment; (v) generating a signal being indicative of the one or more final p-values; and (vi) outputting the signal.

The data processing system of the previous combination may further include a clock being adapted for monitoring, for each of the one or more comparisons, an amount of time elapsing during the start of the at least one EXACT, non-parametric, statistical hypothesis test on the pre-clinical data, wherein the application program is further adapted for determining whether the amount of time exceeds a predetermined threshold.

In accordance with at least one further aspect of the present invention, the methods and apparatus described above may be achieved utilizing suitable hardware, such as that illustrated in the figures. Such hardware may be implemented utilizing any of the known technologies, such as commercially available or custom digital circuitry, any of the known processors that are operable to execute software and/or firmware programs, one or more programmable digital devices or systems, such as programmable read only memories (PROMs), programmable array logic devices (PALs), etc. Furthermore, although the apparatus illustrated in the figures are shown as being partitioned into certain functional blocks, such blocks may be implemented by way of separate circuitry and/or combined into one or more functional units. Still further, the various aspects of the invention may be implemented by way of software and/or firmware program(s) that may be stored on suitable storage medium or media (such as floppy disk(s), memory chip(s), etc.) for transportability and/or distribution.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method, comprising:
receiving pre-clinical data measured during drug treatment of a plurality of mammals including at least two treatment groups;
performing at least one EXACT, non-parametric, statistical hypothesis test comparing the pre-clinical data for the at least two treatment groups; and
performing a Multiple Comparison Procedure (MCP) on a result of the EXACT, non-parametric, statistical hypothesis test for at least two comparisons resulting from comparing the pre-clinical data,
wherein the EXACT, non-parametric, statistical hypothesis test and the MCP are conducted to produce one or more p-values, each p-value representing whether an associated one of the treatment groups has experienced a statistically significant improvement or decline in one or more conditions of the mammals associated with the treatment.

2. The method of claim 1, wherein the EXACT, non-parametric, statistical hypothesis test is taken from the group consisting of: the EXACT Mann-Whitney test, and the EXACT Kruskal-Wallis test.

3. The method of claim 1, wherein the EXACT, non-parametric, statistical hypothesis test is the EXACT Mann-Whitney test.

4. The method of claim 1, wherein the MCP is taken from the group consisting of the Holm-Bonferroni Correction, the Bonferroni Correction, the false discovery rate (FDR) correction, and the Benjamini-Hochberg Correction.

5. The method of claim 1, wherein the MCP is the Holm-Bonferroni Correction test.

6. The method of claim 1, further comprising:
monitoring an amount of time elapsing during the performance of the EXACT, non-parametric, statistical hypothesis test on the pre-clinical data; and determining whether the amount of time exceeds a predetermined threshold.

7. The method of claim 6, further comprising interrupting the performance of the EXACT, non-parametric, statistical hypothesis test on the pre-clinical data of one or more of the comparisons when the determination is in the affirmative.

8. The method of claim 7, further comprising:
performing a Monte Carlo simulation/estimation method of statistical analysis on the pre-clinical data of the one or more of the comparisons, after interrupting the performance of the EXACT, non-parametric, statistical hypothesis test; and
performing the MCP on results of at least one of the EXACT, non-parametric, statistical hypothesis test and the Monte Carlo simulation method for the at least two comparisons to produce the one or more p-values.

9. A method, comprising:
receiving pre-clinical data measured during drug treatment of a plurality of mammals including at least two treatment groups;
performing at least one EXACT, non-parametric, statistical hypothesis test comparing the pre-clinical data for the at least two treatment groups;
monitoring an amount of time elapsing during the performance of the EXACT, non-parametric, statistical hypothesis test on the pre-clinical data;
determining whether the amount of time exceeds a predetermined threshold;
completing the performance of the EXACT, non-parametric, statistical hypothesis test on the pre-clinical data when the determination is in the negative, and interrupting the performance of the EXACT, non-parametric, statistical hypothesis test on the pre-clinical data when the determination is in the affirmative;
performing a Monte Carlo simulation method of statistical analysis on the pre-clinical data of at least one of the comparisons, if the determination is in the affirmative and the performance of the EXACT, non-parametric, statistical hypothesis test is interrupted;
performing a Multiple Comparison Procedure (MCP) on the results of at least one of the EXACT, non-parametric, statistical hypothesis test and the Monte Carlo simulation method for at least two comparisons,
wherein the EXACT, non-parametric, statistical hypothesis test, the Monte Carlo simulation method, and the MCP are conducted to produce one or more p-values, each p-value representing whether an associated one of the treatment groups has experienced a statistically significant improvement or decline in one or more conditions of the mammals associated with the treatment.

10. An apparatus, including a processor operating to perform actions in response to executing computer program instructions, and a non-transitory, computer-readable storage medium containing the computer program instructions, the actions comprising:
receiving pre-clinical data measured during drug treatment of a plurality of mammals including at least two treatment groups;
performing at least one EXACT, non-parametric, statistical hypothesis test comparing the pre-clinical data for the at least two treatment groups; and
performing a Multiple Comparison Procedure (MCP) on a result of the EXACT, non-parametric, statistical hypothesis test for at least two comparisons,
wherein the EXACT, non-parametric, statistical hypothesis test and the MCP are conducted to produce one or more p-values, each p-value representing whether an associated one of the treatment groups has experienced a statistically significant improvement or decline in one or more conditions of the mammals associated with the treatment.

11. The apparatus of claim 10, wherein the EXACT, non-parametric, statistical hypothesis test is taken from the group consisting of: the EXACT Mann-Whitney test, and the EXACT Kruskal-Wallis test.

12. The apparatus of claim 10, wherein the EXACT, non-parametric, statistical hypothesis test is the EXACT Mann-Whitney test.

13. The apparatus of claim 10, wherein the MCP is taken from the group consisting of the Holm-Bonferroni Correction, the Bonferroni Correction, the false discovery rate (FDR) correction, and the Benjamini-Hochberg Correction.

14. The apparatus of claim 10, wherein the MCP is the Holm-Bonferroni Correction.

15. The apparatus of claim 10, the actions further comprising:
monitoring an amount of time elapsing during the performance of the EXACT, non-parametric, statistical hypothesis test on the pre-clinical data; and
determining whether the amount of time exceeds a predetermined threshold.

16. The apparatus of claim 15, the actions further comprising interrupting the performance of the EXACT, non-parametric, statistical hypothesis test on the pre-clinical data of one or more of the comparisons when the determination is in the affirmative.

17. The apparatus of claim 16, the actions further comprising:
performing a Monte Carlo simulation/estimation method of statistical analysis on the pre-clinical data of the one or more of the comparisons, after interrupting the performance of the EXACT, non-parametric, statistical hypothesis test; and
performing the Multiple Comparison Procedure (MCP) on results of at least one of the EXACT, non-parametric, statistical hypothesis test and the Monte Carlo simulation method for the at least two comparisons to produce the one or more p-values.

18. An apparatus including a processor operating to perform actions in response to executing computer program instructions, and a non-transitory, computer-readable storage medium containing the computer program instructions, the actions comprising:
receiving pre-clinical data measured during drug treatment of a plurality of mammals including at least two treatment groups;
performing at least one EXACT, non-parametric, statistical hypothesis test comparing the pre-clinical data for the at least two treatment groups;
monitoring an amount of time elapsing during the performance of the EXACT, non-parametric, statistical hypothesis test on the pre-clinical data;
determining whether the amount of time exceeds a predetermined threshold;
completing the performance of the EXACT, non-parametric, statistical hypothesis test on the pre-clinical data when the determination is in the negative, and interrupting the performance of the EXACT, non-parametric, statistical hypothesis test on the pre-clinical data of one or more comparisons when the determination is in the affirmative;
performing a Monte Carlo simulation method of statistical analysis on the pre-clinical data of the one or more comparisons, if the determination is in the affirmative and the performance of the EXACT, non-parametric, statistical hypothesis test is interrupted;

performing a Multiple Comparison Procedure (MCP) on results of at least one of the EXACT, non-parametric, statistical hypothesis test and the Monte Carlo simulation method for at least two comparisons, wherein the EXACT, non-parametric, statistical hypothesis test, or the Monte Carlo simulation method, and the MCP are conducted to produce one or more p-values, each p-value representing whether an associated one of the treatment groups has experienced a statistically significant improvement or decline in one or more conditions of the mammals associated with the treatment.

19. The apparatus of claim 18, wherein:

the at least two treatment groups include at least a control group and at least two further treatment groups; and the apparatus operates to query a user of the apparatus to select which treatment groups are to be compared using the EXACT, non-parametric, statistical hypothesis test, or the Monte Carlo simulation method, and the MCP.

20. The apparatus of claim 19, wherein the apparatus operates to query a user of the apparatus to select the predetermined threshold.

* * * * *